United States Patent [19]

Madej

[11] Patent Number: 5,476,442
[45] Date of Patent: Dec. 19, 1995

[54] ARTICULATED KNEE PROTECTION APPARATUS

[76] Inventor: Michael W. Madej, 2 S. 738 Timber Dr., Warrenville, Ill. 60555

[21] Appl. No.: 306,581

[22] Filed: Sep. 15, 1994

[51] Int. Cl.⁶ ..................................................... A61F 5/00
[52] U.S. Cl. .............................. 602/26; 602/20; 607/108; 607/112; 607/114
[58] Field of Search .............................. 2/16, 22, 23, 24, 2/26; 602/5, 16, 23, 26, 60, 61, 62, 20; 607/108, 109, 110, 111, 112, 113, 114

[56] References Cited

U.S. PATENT DOCUMENTS

| | | |
|---|---|---|
| 3,817,244 | 6/1974 | Taylor ........................................ 602/26 |
| 3,900,035 | 8/1975 | Welch et al. ............................. 607/108 |
| 4,527,566 | 7/1985 | Abare . |
| 4,556,055 | 12/1985 | Bonner, Jr. . |
| 4,592,358 | 6/1986 | Westplate . |
| 4,628,932 | 12/1986 | Tampa . |
| 4,676,247 | 6/1987 | Van Cleve . |
| 4,688,572 | 8/1987 | Hubbard et al. . |
| 4,753,240 | 6/1988 | Sparks . |
| 4,899,749 | 2/1990 | Laroco . |
| 4,972,832 | 11/1990 | Trapini et al. . |
| 5,148,804 | 9/1992 | Hill et al. ................................. 607/108 |
| 5,304,216 | 4/1994 | Wallace ................................... 607/112 |

FOREIGN PATENT DOCUMENTS 8604810 8/1986 WIPO ..................................... 607/108

Primary Examiner—Stephen R. Crow
Assistant Examiner—Kim M. Lee

[57] ABSTRACT

An articulated limb protection apparatus includes a first heat exchange assembly adapted to contact a first portion of a wearer's limb on a first side of a wearer's joint. A second heat exchange assembly is adapted to contact a second portion of the wearer's limb on a second side of the wearer's joint. A hinge assembly is connected between the first heat exchange assembly and the second heat exchange assembly and forms an articulated connection between the first heat exchange assembly and the second heat exchange assembly. A first strap assembly is connected to the first heat exchange assembly and is adapted to encompass a portion of the wearer's limb on the first side of the joint when the first strap assembly is in a closed orientation. A second strap assembly is connected to the second heat exchange assembly and is adapted to encompass a portion of the wearer's limb on the second side of the joint when the second strap assembly is in a closed orientation. The hinge assembly permits the first heat exchange assembly to rotate around the second heat exchange assembly when the first portion of the wearer's limb on the first side of the joint is rotated around the joint with respect to the second portion of the limb on the second side of the joint. A third heat exchange assembly can be connected between the first strap assembly and the second strap assembly.

3 Claims, 3 Drawing Sheets

ARTICULATED KNEE PROTECTION APPARATUS

BACKGROUND OF THE INVENTION

1. Field of the Invention

The present invention relates generally to protection devices for limbs and, more particularly, to a protection device especially adapted for protecting a wearer's knee.

2. Description of the Prior Art

Limbs are often in need of protection from trauma. Joints such as wrists, elbows, ankles, and knees are especially susceptible to injury, and injured joints are in special need of therapeutic treatment. One form of therapeutic treatment that is often employed is the application of cold temperatures, most often in the form of ice. The direct application of ice has a clear disadvantage in the liquid water that results when the ice melts. In this respect, it would be desirable if cold temperatures can be applied to injured joints without causing a flow of liquid water resulting from melting ice.

When an injury to a joint occurs, the quicker that cold temperatures are applied to the injured joint, the better in order to keep swelling down. Conventional ice packs take quite a bit of time to get ready and apply when minutes and even seconds are important. Conventional ice packs are generally secured to a joint with elastic bandages which are wrapped around both the injured joint and the ice pack. The wrapped process is especially time consuming. In this respect, it would be desirable if cold temperatures can be applied to injured joints without the need for wrapping with an elastic bandage.

Conventional ice packs are often big and clumsy and often fit loosely without providing an even distribution of cold to an injured area. In this respect, it would be desirable if cold temperatures can be applied to injured joints with a tight fit and with an even distribution of cold to the injured area.

There may be some injuries to a joint for which treatment is application of cold temperatures along with bending of the joint in a normal way. However, when a conventional ice pack and an elastic bandage are employed, there may be substantial difficulty in having the joint bend in the normal way. In this respect, it would be desirable if cold temperatures can be applied to an injured joint while permitting the joint to bend in a normal way.

There may be times when an injury is sustained near a joint, but not actually on the joint. However, if a conventional ice pack and elastic bandage are employed, the proximity of the joint may cause the joint to be prevented from bending in a normal way even though the joint itself is not injured. In this respect, it would be desirable if cold temperatures can be applied to an injured area near a joint without preventing normal bending of the nearby joint.

To treat an injured joint or an injured area near an uninjured joint of a limb with cold temperatures, it is often desirable to substantially encompass the limb areas in the vicinity of the joint with cold temperatures. For example, if an injury is sustained on the front side of the limb, it may be desirable to apply cold temperatures to both the front and rear sides of the limb.

In a number of popular sports, knee injuries are especially common. In this respect, it would be desirable if cold temperatures can be applied to injured knees without causing a flow of liquid water resulting from melting ice, without the need for wrapping the knee with an elastic bandage, with using a tight fit, with providing an even distribution of cold to the injured area, with permitting the knee to bend in a normal way, and with substantially encompassing the knee and areas is the vicinity of the knee with cold temperatures.

Thus, while it is well known to use ice packs on limbs and joints, there is presently a need for an articulated knee protection apparatus which has the following combination of desirable features: (1) permits cold temperatures to be applied to injured joints without causing a flow of liquid water resulting from melting ice; (2) permits cold temperatures to be applied to injured joints without the need for wrapping the joints with an elastic bandage; (3) permits cold temperatures to be applied to injured joints with a tight fit and with an even distribution of cold to the injured area; (4) permits cold temperatures to be applied to an injured joint while permitting the joint to bend in a normal way; (5) permits cold temperatures to be applied to an injured area near a joint without preventing normal bending of the nearby joint; (6) provides for substantially encompassing the limb areas in the vicinity of the joint with cold temperatures; and (7) permits cold temperatures to be applied to injured knees without causing a flow of liquid water resulting from melting ice, without the need for wrapping the knee with an elastic bandage, with using a tight fit, with providing an even distribution of cold to the injured area, with permitting the knee to bend in a normal way, and with substantially encompassing the knee and areas is the vicinity of the knee with cold temperatures.

The foregoing desired characteristics are provided by the unique articulated knee protection apparatus of the present invention as will be made apparent from the following description thereof. Other advantages of the present invention over the prior art also will be rendered evident.

SUMMARY OF THE INVENTION

To achieve the foregoing and other advantages, the present invention, briefly described, provides an articulated limb protection apparatus which includes a first heat exchange assembly adapted to contact a first portion of a wearer's limb on a first side of a wearer's joint. A second heat exchange assembly is adapted to contact a second portion of the wearer's limb on a second side of the wearer's joint. A hinge assembly is connected between the first heat exchange assembly and the second heat exchange assembly and forms an articulated connection between the first heat exchange assembly and the second heat exchange assembly. A first strap assembly is connected to the first heat exchange assembly and is adapted to encompass a portion of the wearer's limb on the first side of the joint when the first strap assembly is in a closed orientation. A second strap assembly is connected to the second heat exchange assembly and is adapted to encompass a portion of the wearer's limb on the, second side of the joint when the second strap assembly is in a closed orientation. The hinge assembly permits the first heat exchange assembly to rotate around the second heat exchange assembly when the first portion of the wearer's limb on the first side of the joint which is in contact with the first heat exchange assembly is rotated around the joint with respect to the second portion of the limb on the second side of the joint which is in contact with the second heat exchange assembly.

A third heat exchange assembly can be connected between the first strap assembly and the second strap assembly.

The hinge assembly includes a pair of first hinge portions attached to the first heat exchange assembly. A pair of second hinge portions is attached to the second heat exchange assembly. A pair of hinge pins are provided wherein each hinge pin is connected between a respective first hinge portion and a respective second hinge portion.

The first strap assembly includes a pair of first strap portions adapted for being separated from each other when in an open orientation to encompass the first portion of the limb and adapted for being secured to each other when in a closed orientation to secure the first strap assembly to the limb. The second strap assembly includes a pair of second strap portions adapted for being separated from each other when in an open orientation to encompass the second portion of the limb and adapted for being secured to the each other when in a closed orientation to secure the second strap assembly to the limb.

The first heat exchange assembly includes a concave first inner side adapted to contact a convex portion of the wearer's limb on the first side of the joint, and the second heat exchange assembly includes a concave second inner side adapted to contact a convex portion of the wearer's limb on the second side of the joint.

One of the pair of first strap portions includes a quantity of hook fastener material, and one of the pair of first strap portions includes a quantity of complementary loop fastener material. One of the pair of second strap portions includes a quantity of hook fastener material, and one of the pair of second strap portions includes a quantity of complementary loop fastener material.

The first heat exchange assembly includes a first outer housing connected to the first strap assembly, and a first inner heat-exchange-material container contained within the first outer housing. Similarly, the second heat exchange assembly includes a second outer housing is connected to the second strap assembly, and a second inner heat-exchange-material container contained within the second outer housing.

The above brief description sets forth rather broadly the more important features of the present invention in order that the detailed description thereof that follows may be better understood, and in order that the present contributions to the art may be better appreciated. There are, of course, additional features of the invention that will be described hereinafter and which will be for the subject matter of the claims appended hereto.

In this respect, before explaining a preferred embodiment of the invention in detail, it is understood that the invention is not limited in its application to the details of the construction and to the arrangements of the components set forth in the following description or illustrated in the drawings. The invention is capable of other embodiments and of being practiced and carried out in various ways. Also, it is to be understood, that the phraseology and terminology employed herein are for the purpose of description and should not be regarded as limiting.

As such, those skilled in the art will appreciate that the conception, upon which disclosure is based, may readily be utilized as a basis for designing other structures, methods, and systems for carrying out the several purposes of the present invention. It is important, therefore, that the claims be regarded as including such equivalent constructions insofar as they do not depart from the spirit and scope of the present invention.

It is therefore an object of the present invention to provide a new and improved articulated knee protection apparatus which has all of the advantages of the prior art and none of the disadvantages.

It is another object of the present invention to provide a new and improved articulated knee protection apparatus which may be easily and efficiently manufactured and marketed.

It is a further object of the present invention to provide a new and improved articulated knee protection apparatus which is of durable and reliable construction.

An even further object of the present invention is to provide a new and improved articulated knee protection apparatus which is susceptible of a low cost of manufacture with regard to both materials and labor, and which accordingly is then susceptible of low prices of sale to the consuming public, thereby making such articulated knee protection apparatus available to the buying public.

Still yet a further object of the present invention is to provide a new and improved articulated knee protection apparatus which permits cold temperatures to be applied to injured joints without causing a flow of liquid water resulting from melting ice.

Still another object of the present invention is to provide a new and improved articulated knee protection apparatus that permits cold temperatures to be applied to injured joints without the need for wrapping the joints with an elastic bandage.

Yet another object of the present invention is to provide a new and improved articulated knee protection apparatus which permits cold temperatures to be applied to injured joints with a tight fit and with an even distribution of cold to the injured area.

Even another object of the present invention is to provide a new and improved articulated knee protection apparatus that permits cold temperatures to be applied to an injured joint while permitting the joint to bend in a normal way.

Still a further object of the present invention is to provide a new and improved articulated knee protection apparatus which permits cold temperatures to be applied to an injured area near a joint without preventing normal bending of the nearby joint.

Yet another object of the present invention is to provide a new and improved articulated knee protection apparatus that provides for substantially encompassing the limb areas in the vicinity of the joint with cold temperatures.

Still another object of the present invention is to provide a new and improved articulated knee protection apparatus which permits cold temperatures to be applied to injured knees without causing a flow of liquid water resulting from melting ice, without the need for wrapping the knee with an elastic bandage, with using a tight fit, with providing an even distribution of cold to the injured area, with permitting the knee to bend in a normal way, and with substantially encompassing the knee and areas is the vicinity of the knee with cold temperatures.

These together with still other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and the above objects as well as objects other than those set forth above will become more apparent after a study of the following detailed description thereof. Such description makes reference to the annexed drawing wherein.

DESCRIPTION OF THE PREFERRED EMBODIMENT

Figure 1:
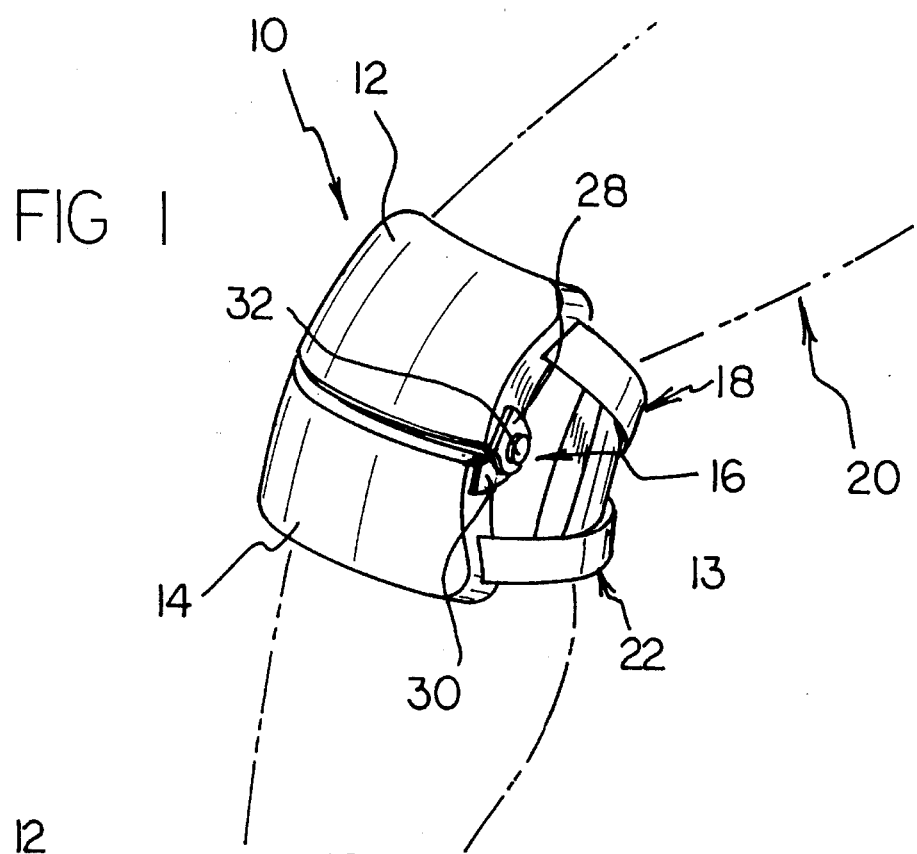
FIG. 1 is a perspective view showing a preferred embodiment of the articulated knee protection apparatus of the invention in position on a wearer's leg.
Figure 2:
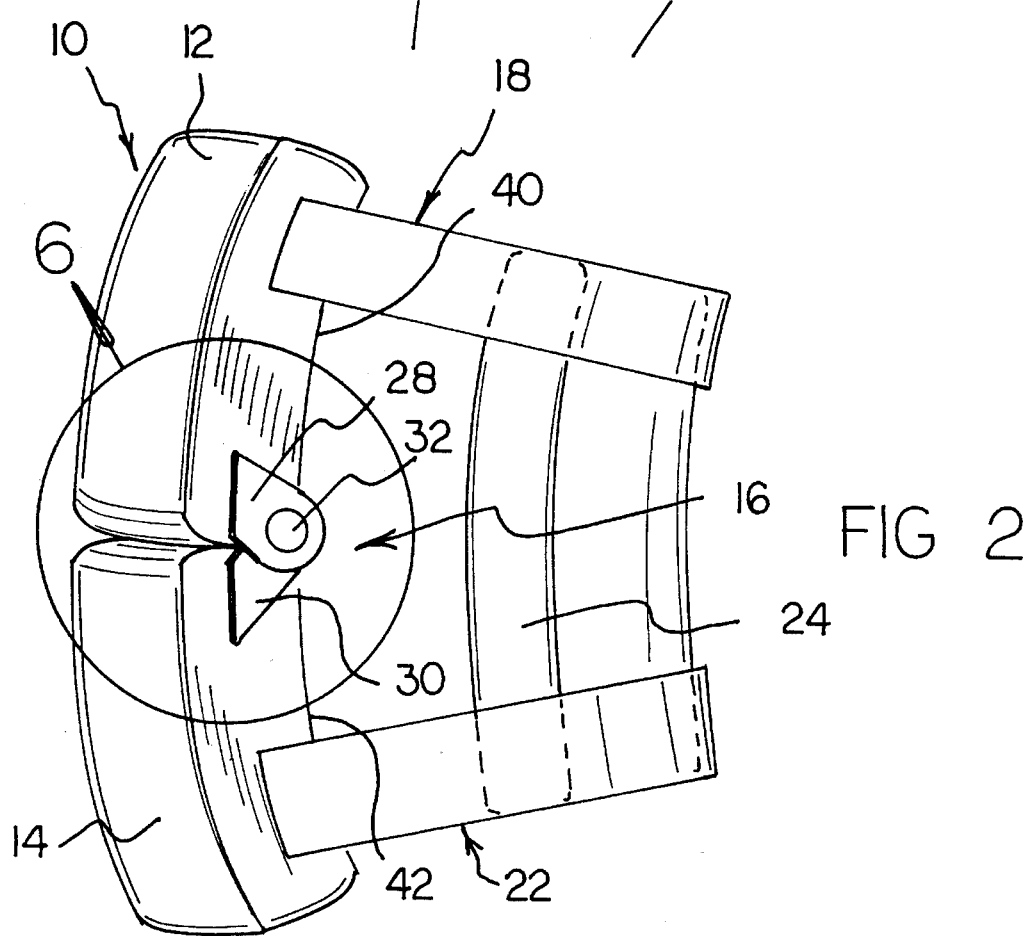
FIG. 2 is an enlarged side view of the embodiment of the articulated knee protection apparatus shown in FIG. 1 removed from the leg and in a closed orientation.
Figure 3:
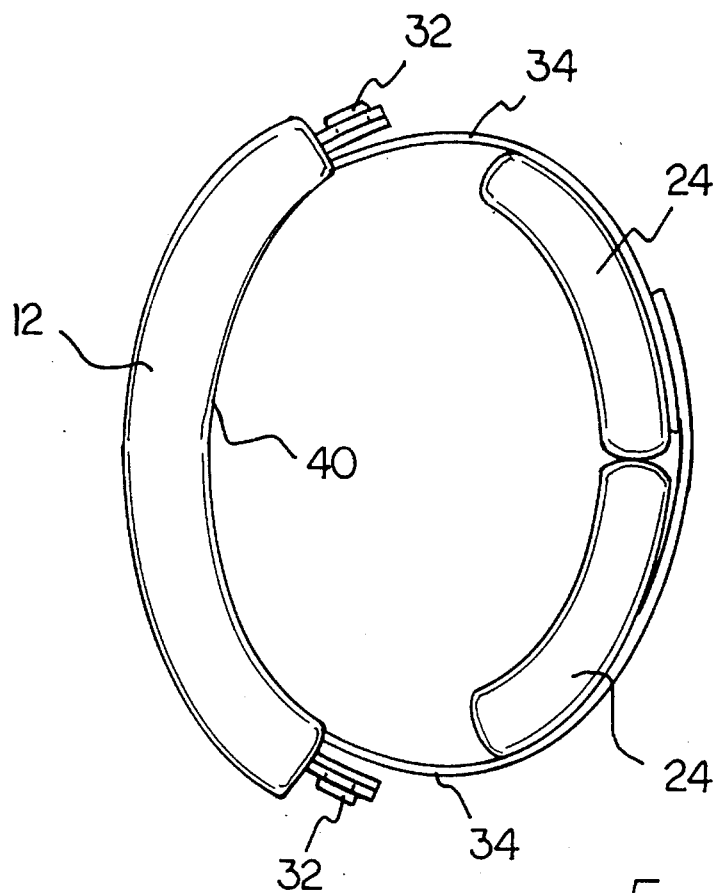
FIG. 3 is a top view of the embodiment of the articulated knee protection apparatus of FIG. 2.
Figure 4:
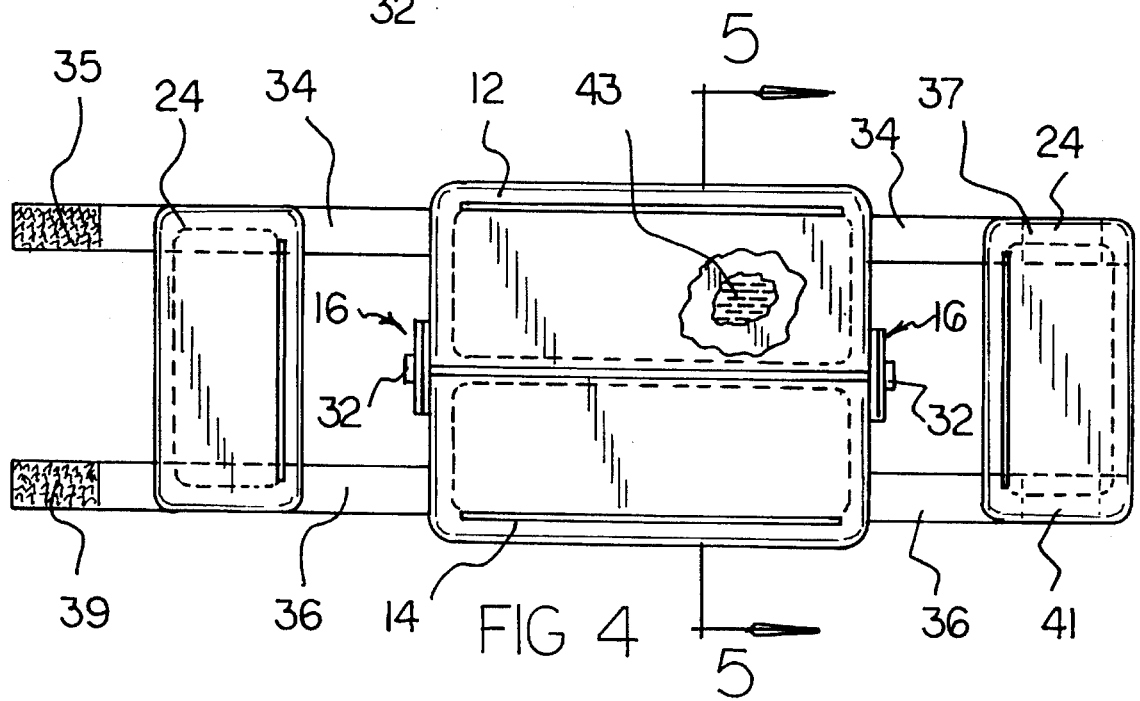
FIG. 4 is a front view of the embodiment of the invention shown in FIG. 3 shown in an open orientation.

With reference to the drawings, a new and improved articulated knee protection apparatus embodying the principles and concepts of the present invention will be described.

Turning to FIGS. 1–6, there is shown an exemplary embodiment of the articulated knee protection apparatus of the invention generally designated by reference numeral 10. In its preferred form, articulated knee protection apparatus 10 includes a first heat exchange assembly 12 adapted to contact a first portion of a wearer's limb 20 on a first side of a wearer's joint 13. A second heat exchange assembly 14 is adapted to contact a second portion of the wearer's limb 20 on a second side of the wearer's joint 13. A hinge assembly 16 is connected between the first heat exchange assembly 12 and the second heat exchange assembly 14 and forms an articulated connection between the first heat exchange assembly 12 and the second heat exchange assembly 14. A first strap assembly 18 is connected to the first heat exchange assembly 12 and is adapted to encompass a portion of the wearer's limb 20 on the first side of the joint 13 when the first strap assembly 18 is in a closed orientation. A second strap assembly 22 is connected to the second heat exchange assembly 14 and is adapted to encompass a portion of the wearer's limb 20 on the second side of the joint 13 when the second strap assembly 22 is in a closed orientation. The hinge assembly 16 permits the first heat exchange assembly 12 to rotate around the second heat exchange assembly 14 when the first portion of the wearer's limb 20 on the first side of the joint 13 which is in contact with the first heat exchange assembly 12 is rotated around the joint 13 with respect to the second portion of the limb 20 on the second side of the joint 13 which is in contact with the second heat exchange assembly 14.

A third heat exchange assembly 24 is connected between the first strap assembly 18 and the second strap assembly 22. A plurality of third heat exchange assemblies 24 can be used. The third heat exchange assemblies 24 can be attached to the respective first strap assembly 18 and second strap assembly 22 by of an adhesive, by sewn stitches, or by other suitable attaching means such as hook and loop VELCRO(TM) material. Alternatively, the third heat exchange assemblies 24 can be secured to the limb 20 of the wearer by compressive pressure exerted by the first strap portions 34 and the second strap portions 36 when the first strap portions 34 and the second strap portions 36 are in a closed orientation.

A third heat exchange assembly 24 is connected between the first strap assembly 18 and the second strap assembly 22. The third heat exchange assembly 24 is adapted to contact a third portion of the wearer's limb 20 on the first side of the wearer's joint on a rear side of the wearer's limb 20 and is adapted to contact a fourth portion of the wearer's limb 20 on the second side of the wearer's joint on the rear side of the wearer's limb 20. The first heat exchange assembly 12, the second heat exchange assembly 14, and the third heat exchange assembly 24, in combination, substantially encompass the wearer's limb areas in the vicinity of the wearer's joint 13.

The hinge assembly 16 includes a pair of first hinge portions 28 attached to the first heat exchange assembly 12. A pair of second hinge portions 30 is attached to the second heat exchange assembly 14. A pair of hinge pins 32 are provided wherein each hinge pin 32 is connected between a respective first hinge portion 28 and a respective second hinge portion 30.

The first strap assembly 18 includes a pair of first strap portions 34 adapted for being separated from each other when in an open orientation to encompass the first portion of the limb 20 and adapted for being secured to each other when in a closed orientation to secure the first strap assembly 18 to the limb 20. The second strap assembly 22 includes a pair of second strap portions 36 adapted for being separated from each other when in an open orientation to encompass the second portion of the limb 20 and adapted for being secured to the each other when in a closed orientation to secure the second strap assembly 22 to the limb 20.

When the first strap assembly 18 and the second strap assembly 22 are in a closed orientation, the first heat exchange assembly 12, the second heat exchange assembly 14, and the third heat exchange assemblies 24 can be held tightly against the limb 20 of the wearer. Such tight holding of the heat exchange assemblies against the limb 20 can prevent the first heat exchange assembly 12 and the second heat exchange assembly 14 from shifting position or moving when secured to the limb 20.

The first heat exchange assembly 12 includes a concave first inner side 40 adapted to contact a convex portion of the wearer's limb 20 on the first side of the joint 13, and the second heat exchange assembly 14 includes a concave second inner side 42 adapted to contact a convex portion of the wearer's limb 20 on the second side of the joint 13. The concave first inner side 40 and the concave second inner side 42 can be molded for specific limbs and joints. For example, they can be molded to fit the knee, the ankle, and the wrist and even the shoulder.

One of the pair of first strap portions 34 includes a quantity of hook fastener material 35, and one of the pair of first strap portions 34 includes a quantity of complementary loop fastener material 37. One of the pair of second strap portions 36 includes a quantity of hook fastener material 39, and one of the pair of second strap portions 36 includes a quantity of complementary loop fastener material 41. The hook and loop material can be VELCRO™ material.

Figure 5:
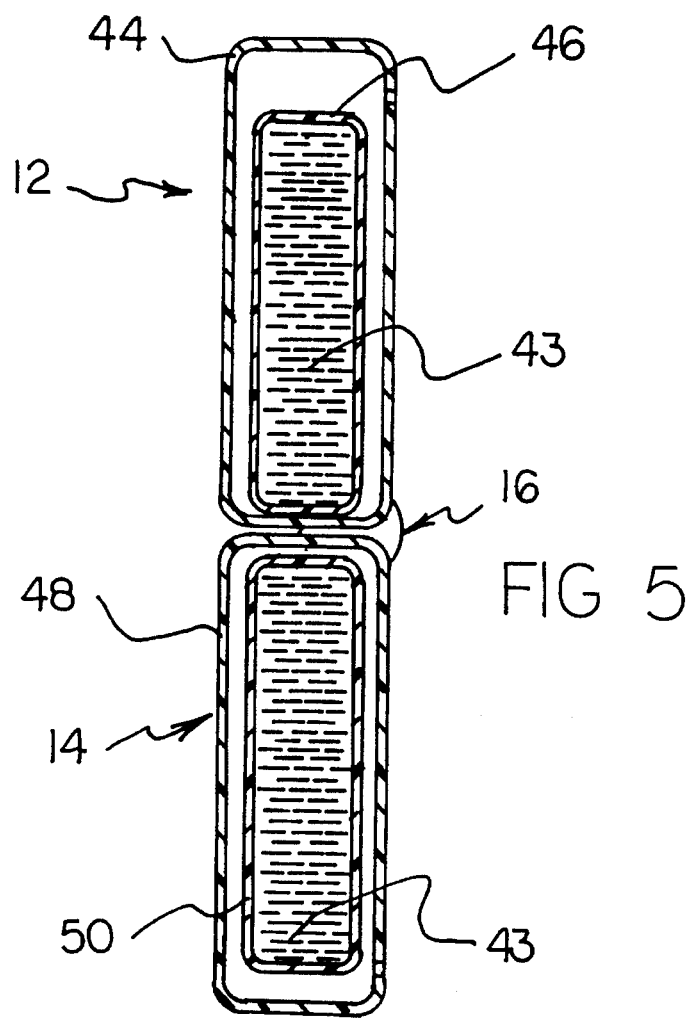
FIG. 5 is an enlarged cross-sectional view of the embodiment of the invention shown in FIG. 4 taken along line 5—5 of FIG. 4.
Figure 6:
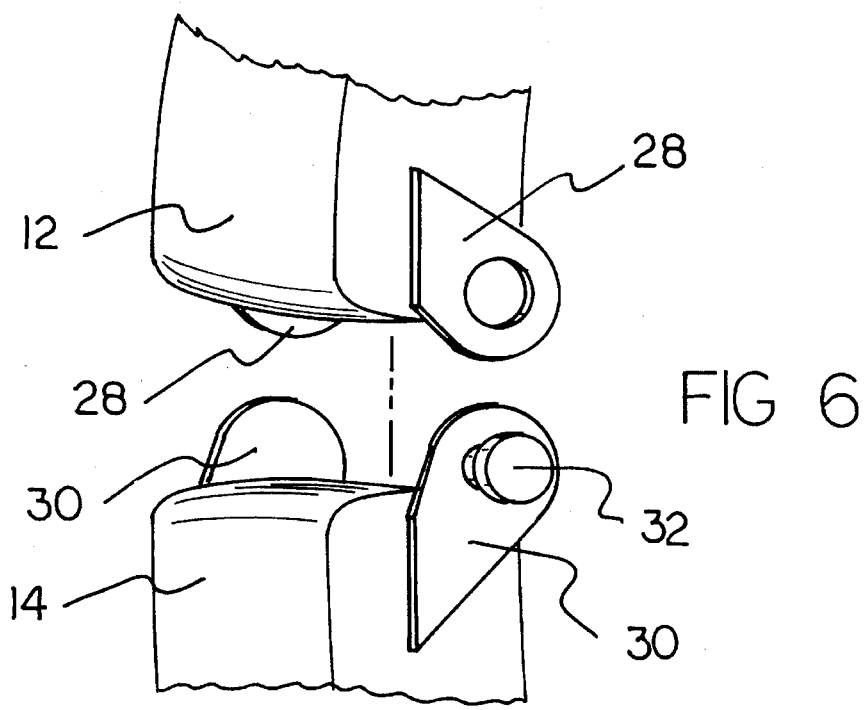
FIG. 6 is an enlarged, partially exploded view of the circled portion 6 of FIG. 2.

As shown in FIG. 5, the first heat exchange assembly 12 includes a first outer housing 44 is connected to the first strap assembly 18, and a first inner heat-exchange-material container 46 contained within the first outer housing 44. Similarly, the second heat exchange assembly 14 includes a second outer housing 48 is connected to the second strap assembly 22, and a second inner heat-exchange-material container 50 contained within the second outer housing 48. The heat-exchange material is ethylene-glycol-based liquid

43.

In use, the articulated knee protection apparatus 10 of the invention is easily attached to a wearer. In a very rapid manner, the first heat exchange assembly 12 and the second heat exchange assembly 14 can be placed against the first portion of a wearer's limb 20 on a first side of a wearer's joint 13 and the second portion of the wearer's limb 20 on a second side of the wearer's joint 13, respectively. In an open orientation, the first strap portions 34 are made to encompass the first portion of a wearer's limb 20 on a first side of a wearer's joint 13. Then, the first strap portions 34 are connected together in a closed orientation. In an open orientation, the second strap portions 36 are made to encompass the second portion of the wearer's limb 20 on a second side of the wearer's joint 13. Then, the second strap portions 36 are connected together in a closed orientation.

The entire articulated knee protection apparatus 10 of the invention can be stored in a cold environment, such as a refrigerator or freezer. Alternatively, cold heat-exchange material can be loaded into the respective first heat exchange assembly 12 and second heat exchange assembly 14 just before use.

The first outer housing 44 and the second outer housing 48 can be made from plastic materials or from insulated cloth materials forming a jacket around the heat-exchange materials. The heat-exchange material can be a variety of materials which includes water, ice, and ethylene-glycol-based blue ice. The first heat exchange assembly 12 and the second heat exchange assembly 14 can be sealed units or can have openable and closable closures for filling or emptying heat-exchange material from the respective heat exchange assemblies.

The articulated knee protection apparatus 10 of the invention can be used by players of almost any sport such as baseball, basketball, football, tennis, and soccer, among others. The articulated knee protection apparatus 10 of the invention can be especially useful for treating twisted knees, sprained ankles, and sprained wrists.

The components of the articulated knee protection apparatus of the invention can be made from inexpensive and durable metal and plastic materials.

As to the manner of usage and operation of the instant invention, the same is apparent from the above disclosure, and accordingly, no further discussion relative to the manner of usage and operation need be provided.

It is apparent from the above that the present invention accomplishes all of the objects set forth by providing a new and improved articulated knee protection apparatus that is low in cost, relatively simple in design and operation, and which may advantageously be used to permit cold temperatures to be applied to injured joints without causing a flow of liquid water resulting from melting ice. With the invention, an articulated knee protection apparatus is provided which permits cold temperatures to be applied to injured joints without the need for wrapping the joints with an elastic bandage. With the invention, an articulated knee protection apparatus is provided which permits cold temperatures to be applied to injured joints with a tight fit and with an even distribution of cold to the injured area. With the invention, an articulated knee protection apparatus is provided which permits cold temperatures to be applied to an injured joint while permitting the joint to bend in a normal way. With the invention, an articulated knee protection apparatus is provided which permits cold temperatures to be applied to an injured area near a joint without preventing normal bending of the nearby joint. With the invention, an articulated knee protection apparatus provides for substantially encompassing the limb areas in the vicinity of the joint with cold temperatures. With the invention, an articulated knee protection apparatus is provided which permits cold temperatures to be applied to injured knees without causing a flow of liquid water resulting from melting ice, without the need for wrapping the knee with an elastic bandage, with using a tight fit, with providing an even distribution of cold to the injured area, with permitting the knee to bend in a normal way, and with substantially encompassing the knee and areas is the vicinity of the knee with cold temperatures.

Thus, while the present invention has been shown in the drawings and fully described above with particularity and detail in connection with what is presently deemed to be the most practical and preferred embodiment(s) of the invention, it will be apparent to those of ordinary skill in the art that many modifications thereof may be made without departing from the principles and concepts set forth herein, including, but not limited to, variations in size, materials, shape, form, function and manner of operation, assembly and use.

Hence, the proper scope of the present invention should be determined only by the broadest interpretation of the appended claims so as encompass all such modifications as well as all relationships equivalent to those illustrated in the drawings and described in the specification.

Finally, it will be appreciated that the purpose of the foregoing Abstract provided at the beginning of this specification is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. Accordingly, the Abstract is neither intended to define the invention or the application, which only is measured by the claims, nor is it intended to be limiting as to the scope of the invention in any way.

What is claimed as being new and desired to be protected by Letters Patent of the United States is as follows:

1. An articulated limb protection apparatus, comprising:

a first heat exchange assembly adapted to contact a first portion of a front side of a wearer's limb on a first side of a wearer's joint, a second heat exchange assembly adapted to contact a second portion of the front side of the wearer's limb on a second side of the wearer's joint, a hinge assembly hingedly connecting said first heat exchange assembly and said second heat exchange assembly, said hinge assembly forming an articulated connection between said first heat exchange assembly and said second heat exchange assembly, a first strap assembly connected to said first heat exchange assembly, said first strap assembly adapted to encompass a portion of the wearer's limb on the first side of the joint when said first strap assembly is in a closed orientation, a second strap assembly connected to said second heat exchange assembly, said second strap assembly adapted to encompass a portion of the wearer's limb on the second side of the joint when said second strap assembly is in a closed orientation, and a third heat exchange assembly connected between said first strap assembly and said second strap assembly, wherein said third heat exchange assembly is adapted to contact a third portion of the wearer's limb on the first side of the wearer's joint on a rear side of the wearer's limb and is adapted to contact a fourth portion of the wearer's limb on the second side of the wearer's joint on the rear side of the wearer's limb, wherein said first heat exchange assembly, said second heat exchange assembly, and said third heat exchange assembly, in combination, substantially encompass the wearer's limb areas in the vicinity of the wearer's joint, wherein said hinge assembly permits said first heat exchange assembly to rotate with respect to said second heat exchange assembly when the first portion of the wearer's limb on the first side of the joint which is in contact with said first heat exchange assembly is rotated around the joint with respect to the second portion of the limb on the second side of the joint which is in contact with said second heat exchange assembly, wherein said hinge assembly includes a pair of first hinge portions attached to said first heat exchange assembly, a pair of second hinge portions attached to said second heat exchange assembly, and a pair of hinge pins wherein each hinge pin is connected between a respective first hinge portion and a respective second hinge portion, wherein said first heat exchange assembly includes a concave first inner side adapted to contact a convex portion of the wearer's limb on the first side of the joint, and said second heat exchange assembly includes a concave second inner side adapted to contact a convex portion of the wearer's limb on the second side of the joint, wherein said first strap assembly includes a pair of first strap portions adapted for being separated from each other when in an open orientation to encompass the first portion of the limb and adapted for being secured to each other when in a closed orientation to secure said first strap assembly to the limb, and said second strap assembly includes a pair of second strap portions adapted for being separated from each other when in an open orientation to encompass the second portion of the limb and adapted for being secured to the each other when in a closed orientation to secure said second strap assembly to the limb, and wherein one of said pair of first strap portions includes a quantity of hook fastener material, and one of said pair of first strap portions includes a quantity of complementary loop fastener material, and one of said pair of second strap portions includes a quantity of hook fastener material, and one of said pair of second strap portions includes a quantity of complementary loop fastener material.

2. The apparatus of claim 1 wherein said first heat exchange assembly includes:

a first outer housing connected to said first strap assembly, and a first inner heat-exchange-material container contained within said first outer housing.

3. The apparatus of claim 1 wherein said second heat exchange assembly includes:

a second outer housing connected to said second strap assembly, and a second inner heat-exchange-material container contained within said second outer housing.

\* \* \* \* \*